United States Patent
Bardag-Gorce (10) Patent No.: US 10,736,934 B2
(45) Date of Patent: Aug. 11, 2020

(54) PROTEASOME MODULATION FOR TREATMENT OF CORNEAL DISORDERS

(71) Applicant: The Lundquist Institute, Torrance, CA (US)

(72) Inventor: Fawzia Bardag-Gorce, Torrance, CA (US)

(73) Assignee: The Lundquist Institute for Biomedical Innovation at Harbor-UCLA Medical Center, Torrance, CA (US)

( * ) Notice: Subject to any disclaimer, the term of this patent is extended or adjusted under 35 U.S.C. 154(b) by 0 days.

(21) Appl. No.: 15/775,728

(22) PCT Filed: Nov. 11, 2016

(86) PCT No.: PCT/US2016/061656
§ 371 (c)(1),
(2) Date: May 11, 2018

(87) PCT Pub. No.: WO2017/083741
PCT Pub. Date: May 18, 2017

(65) Prior Publication Data
US 2018/0369316 A1 Dec. 27, 2018

Related U.S. Application Data

(60) Provisional application No. 62/255,338, filed on Nov. 13, 2015.

(51) Int. Cl.
| | |
|---|---|
| A61K 38/05 | (2006.01) |
| A61K 31/222 | (2006.01) |
| A61K 31/426 | (2006.01) |
| A61K 31/407 | (2006.01) |
| A61K 31/495 | (2006.01) |
| A61K 31/7048 | (2006.01) |
| A61K 31/69 | (2006.01) |
| A61K 31/4015 | (2006.01) |
| A61K 31/336 | (2006.01) |
| A61K 31/4439 | (2006.01) |
| A61K 31/5377 | (2006.01) |
| A61P 27/02 | (2006.01) |

(52) U.S. Cl.
CPC ............ *A61K 38/05* (2013.01); *A61K 31/222* (2013.01); *A61K 31/336* (2013.01); *A61K 31/407* (2013.01); *A61K 31/4015* (2013.01); *A61K 31/426* (2013.01); *A61K 31/4439* (2013.01); *A61K 31/495* (2013.01); *A61K 31/5377* (2013.01); *A61K 31/69* (2013.01); *A61K 31/7048* (2013.01); *A61P 27/02* (2018.01)

(58) Field of Classification Search
None
See application file for complete search history.

(56) References Cited

U.S. PATENT DOCUMENTS

| | | |
|---|---|---|
| 2003/0086986 A1 | 5/2003 | Bruijn et al. |
| 2006/0280729 A1 | 12/2006 | Mistry |
| 2013/0324481 A1* | 12/2013 | Wong ................... A61K 9/0048 514/20.5 |

FOREIGN PATENT DOCUMENTS

EP          1 565 193         4/2013

OTHER PUBLICATIONS

Ciechanover, Aaron and Schwartz, Alan L., "THe ubiquitin-proeasome pathway: the complexidty and myriad functions of protein death." Proc. Natl. Acad. Sci. USA (1990) 95 p. 2727-2730.*
Sejpal, Kunjal et al, "Presentation, diagnosis, and management of limbal stem cell deficiency." Middle East. Afr. J. Ophthalmol. (2013) 20(1) p. 5-10.*
Velcade website http://www.velcade.com/understanding-velcade/about-velcade, available Oct. 6, 2014.*
Le Tourneau, Christophe et al, "Dose escalation methods in phase I cancer clinical trials." J. Natl. Cancer Inst. (2009) 101 p. 708-720.*
The dosing information for velcade from Medscape, https://web.archive.org/web/20120411121554/https://reference.medscape.com/drug/velcade-bortezomib-342256, available online 2012.*
International Search Report and Written Opinion of PCT/US16/061656, dated Jan. 10, 2017 (10 pages).
Aswathi et al., "Downregulation of MMP-2 and -9 by Proteasome Inhibition: A Possible Mechanism to Decrease LEC Migration and Prvent Posterior Capsular Opacification," Investigative Ophthalmology & Visual Science, May 2008, vol. 49, No. 5, pp. 1998-2003.
Bardag-Gorce et al., "The proteasome inhibitor, PS-341, causes cytokeratin aggresome formation," Experimental and Molecular Pathology, 2004, vol. 76, pp. 9-16.
Bardag-Gorce et al., "Proteasome inhibitor up regulates liver antioxidative enzymes in rat model of alcoholic liver disease", Experimental and Molecular Pathology 90 (2011) pp. 123-130.
Black et al., "Molecular mechanisms of ALDH3A1-mediated cellular protection against 4-hydroxy-2-nonenal", Free Radical Biology and Medicine, 2012, vol. 52, No. 9, pp. 1937-1944.

(Continued)

*Primary Examiner* — Fred H Reynolds
(74) *Attorney, Agent, or Firm* — Sheppard Mullin Richter & Hampton LLP (57) ABSTRACT

Disclosed herein are methods and compositions useful for preventing or reducing corneal haze of opacification resulting from Limbal Stem Cell Deficiency (LSCD). The invention comprises a method of preventing or treating corneal opacification, comprising administering to a subject a sufficient amount of a proteasome modulator. The invention also comprises a method of preventing or treating corneal opacification, comprising administering to a subject a sufficient amount of a proteasome modulator. In addition, the invention comprises a method of administering to a subject suffering from corneal opacification with a sufficient amount of proteasome modulator, resulting in reduction of Keratin proteins in the cornea of the subject.

7 Claims, 9 Drawing Sheets

(56) References Cited

OTHER PUBLICATIONS

Chen et al, "Ocular aldehyde dehydrogenases: Protection against ultraviolet damage and maintenance of transparency for vision", Progress in Retinal and Eye Research, 2013, vol. 33, pp. 28-33.

Choi et al., "Autophay is induced by raptor degradation via the ubiquitin/proteasome system in granular corneal dystrophy type 2", Biochemical and Biophysical Research Communications, vol. 450, (2014), pp. 1505-1511.

Das et al., "Phenotypic alteration of limbal niche-associated limbal epithelial stem cell deficiency by ulraviolet-B exposure-induced phototoxicity in mice", Biochemistry and Cell Biology, 2013, vol. 91, No. 3, pp. 165-175.

Estey et al., "ALDH3A1: a corneal crystallin with diverse functions", Experimental Eye Research 84 (2007) pp. 3-12.

Han et al., "Long-term outcome and prognostic factor analysis for keratolimbal allografts", Graefes Arch Cin Exp Ophthalmol (2011) 249: pp. 1697-1704.

Hsu et al., "Proteasome Inhibitor Bortezomib Suppresses Nuclear Factor-Kappa B Activiation and Ameliorates Eye Inflammation in Experimental Autoimmune Uveitis", Mediators of Inflammation, vol. 2015, Article ID 847373, 10 pages.

Klinenstein et al., "Decrease in Bilateral Corneal Deposits After Bortezomib/Dexamethasone Chemotherapy in Monoclonal Gammopathy: Case Report", Journal of Analytical Oncology, 2012, vol. 1, 103-106.

Murata, "Diversity and significance of proteasomes in mammals", Biochemistry, 2008, vol. 80, No. 8, pp. 719-732 (in Japanese with English abstract).

Poli et al., "Keratin 13 Immunostaining in Corneal Impression Cytology for the Diagnosis of Limbal Stem Cell Deficiency", Investigative Ophthalmology & Visual Sciences, 2011, vol. 52, No. 13, pp. 9411-9415.

\* cited by examiner

FIG. 1

FIG. 2A Normal Epithelium (NE)

FIG. 2B Diseased Epithelium (DE)

K4 levels 72H after PS341 treatement

PROTEASOME MODULATION FOR TREATMENT OF CORNEAL DISORDERS

CROSS REFERENCE TO RELATED APPLICATIONS

This application is a national stage of International Application No. PCT/US2016/061656 filed Nov. 11, 2016, which claims the benefit of U.S. Provisional Application No. 62/255,338, filed Nov. 13, 2015, the disclosure of which is hereby incorporated by reference.

BACKGROUND OF THE INVENTION

Field of the Invention

Corneal opacification resulting from Limbal Stem Cell Deficiency (LSCD) leads to abnormal accumulation of protein aggregates in the cornea. Keratins are a group of proteins that form intermediate filaments in epithelial cells. They are divided in two groups: type I Keratins (small, acidic, including K9-K20) and type II Keratins (large, neutral to basic, including K1-K8). They are usually found in pairs that include a type I and type II and are highly tissue-specific. Corneal epithelial cells are characterized by the expression of keratins K3/K12 and conjunctival epithelial cells by the expression of keratins K13/K4 (Lin et al., 2010). In the case of LSCD, corneal epithelium keratin expression shifts from K12/K3 to K13/K4 positive cells, which indicates conjunctivalization of the central cornea (Bardag-Gorce et al., 2015 and Poli et al., 2015).

Description of the Related Art

At present, there are few treatments for corneal opacification other than corneal surgery or corneal transplant. Dysfunction of the ubiquitin 26S constitutive proteasome (CPR) has been shown to cause keratin aggregation and accumulation (Bardag-Gorce et al., 2004), indicating the important role of CPR in regulating epithelial cell keratin clearance. The use of proteasome inhibitors or proteasome modulators for preventing or treating corneal opacification or the use of proteasome inhibitors or proteasome modulators for reducing keratin proteins in the cornea has not been described in the art.

SUMMARY OF THE INVENTION

Disclosed herein are methods and compositions useful for preventing or reducing corneal haze or opacification. In certain embodiments, the corneal opacification results from Limbal Stem Cell Deficiency (LSCD). An embodiment of the invention comprises a method of preventing or treating corneal opacification, comprising administering to a subject a sufficient amount of a proteasome modulator. An embodiment of the invention comprises a method of preventing or treating corneal opacification, comprising administering to a subject a sufficient amount of a proteasome modulator. An embodiment of the invention comprises a method of administering to a subject suffering from corneal opacification with a sufficient amount of proteasome modulator resulting in reduction of keratins in the cornea of the subject. An embodiment of the invention comprises a method of administering to a subject suffering from corneal opacification a sufficient amount of proteasome modulator resulting in reduction of Keratin 13 in the cornea of the subject. In an embodiment, the administration results in the reduction of Keratin 4 in the cornea of the subject.

In an embodiment, the method results in the reduction of conjunctival proteins in the cornea of the subject. In yet another embodiment, the method results in the reduction of conjunctival protein, Muc5ac, in the cornea of the subject. In an embodiment, the method results in the reduction of globlet cells on the cornea of the subject. In an embodiment, the method results in increased activity of the CPR more than 72 hours after treatment. In an embodiment, the increased activity of the CPR is more than 20% compared to the activity of the CPR prior to treatment. In an embodiment, the increased activity of the CPR is more than 30% compared to the activity of the CPR prior to treatment. In an embodiment, the increased activity of the CPR is more than 50% compared to the activity of the CPR prior to treatment. In an embodiment, the method results in reduced activity of the IPR. An embodiment of the invention results in the reduction of inflammation in the cornea of the subject. In an embodiment, the method results in reduced activity of Necrosis Factor Kappa B (NFκB) in the cornea of the subject. In an embodiment, the method results in reduced Interferon Gamma in the cornea of the subject. In an embodiment, the method results in reduced Tumor Necrosis Factor Alpha in the cornea of the subject. In an embodiment, the method results in reduced interleukins in the cornea of the subject. In an embodiment, the method results in reduced opacification in the cornea of the subject. In an embodiment, the method results in improved vision in the subject. Certain embodiments of the invention comprise compositions and methods for the prevention and treatment of eye irritation, redness of the eye tissues or eyelid, swelling of the eye tissues or eye lid, eye discharge, blurred vision and vision loss due to corneal opacification. In certain embodiments, the compositions and methods of the present invention prevent or reduce corneal dystrophies comprising, Fuchs' dystrophy, Keratoconus, Granular dystrophy, Lattice dystrophy and Map-dot-fingerprint dystrophy.

In an embodiment, the subject has had a corneal injury. In an embodiment, the subject has had a corneal injury due to trauma to the eye. In an embodiment, the subject produces fewer or lower quality tears. In an embodiment, the subject has Sjögren's syndrome. In an embodiment, the subject has had an eye infection comprising conjunctivitis, herpes zoster or ocular herpes. In an embodiment, the subject has had or is suffering from keratitis. In certain embodiments the subject has had inflammation of the eye. In certain embodiments, the subject has injured corneal tissues due to an abrasion, object damaging the corneal tissue, use of contact lenses, ultraviolet light, scarring from a burn or chemical irritation.

An embodiment of the invention comprises a method of treating or preventing corneal opacification comprising administration to a subject a sufficient amount of the proteasome inhibitor, PS-341 (Bortezomib/Velcade®). Certain embodiments of the invention comprise a method of treating or preventing corneal opacification comprising administration to a subject a sufficient amount of a proteasome modulator, wherein the proteasome modulator is: MG-132, Bortezomib (PS-341), Dihydroeponemycin, Oprozomib (ONX-0912), MLN2238, Epoxomicin, Carfilzomib (PR-171), ONX-0914 (PR-957), PSI, MG-115, MG-262, AM 114, PI-1840, Chymotrypsin-like (CT-L) inhibitor, MLN9708, CEP-18770, Gliotoxin, Salinosporamide A (NPI-0052, Marizomib), Clasto-Lactacystin β-lactone, Lactacystin, Ixazomib®, oleuropein or derivatives or analogues thereof.

In an embodiment, PS-341 is administered for 24 to 72 hours. In an embodiment, PS-341 is administered for 48 hours. In an embodiment, PS-341 is administered for less than 72 hours. In an embodiment, PS-341 is administered for less than 24 hours. In an embodiment, the PS-341 is administered in a formulation where the concentration of PS-341 is between 2.5 nM and 10 nM. In an embodiment, the PS-341 is administered in a formulation where the concentration of PS-341 is 2.5 nM. In an embodiment, the PS-341 is administered in a formulation in which the concentration of PS-341 is 10 nM. In an embodiment, the PS-341 is administered in a formulation in which the concentration of PS-341 is between 10 nM and 1 µM. In an embodiment, the PS-341 is administered at a dose of 0.00125 to 0.125 mg/mL per kg body weight of the subject. In an embodiment, the PS-341 is administered at a sufficient dose to increase the CPR activity in the subject after 72 hours of treatment more than 20% as compared to prior to treatment. In an embodiment, the PS-341 is administered at a sufficient dose to increase the CPR activity in the subject after 72 hours of treatment more than 30% as compared to prior to treatment. In an embodiment, the PS-341 is administered at a sufficient dose to increase the CPR activity in the subject after 72 hours of treatment more than 60% as compared to CPR activity prior to treatment.

In an embodiment, the proteasome modulator is administered orally. In an embodiment, the proteasome modulator is administered topically. In an embodiment, the proteasome modulator is administered as an ophthalmic solution, ophthalmic suspension, ophthalmic ointment, ophthalmic emulsion or ophthalmic gel. In an embodiment, the proteasome modulator is administered intraocularly.

BRIEF DESCRIPTION OF THE SEVERAL VIEWS OF THE DRAWINGS

These and other features, aspects, and advantages of the present invention will become better understood with regard to the following description, and accompanying drawings, where.

DETAILED DESCRIPTION OF THE INVENTION

Briefly, and as described in more detail below, described herein are methods and compositions useful for reducing corneal opacification resulting from Limbal Stem Cell Deficiency (LSCD). Deficiency in LSCs resulting in cornea haze or opacification leads to blindness in millions of people worldwide. Corneal problems are the fourth leading cause of blindness after glaucoma, cataract, and age-related macular degeneration.

Several features of the current approach should be noted. The method comprises the administration of a proteasome modulator to prevent or treat corneal opacification in subjects with corneal damage and/or suffering from corneal opacification. The method comprises the administration of a proteasome modulator such as, e.g., PS-341 (Bortezomib or Velcade®). The method also comprises administration of PS-341 as an ophthalmic solution in a formulation wherein the concentration of PS-341 is non-toxic and results in the activation of the CPR. The method also comprises administration of PS-341 wherein the administration leads to the reduction of inflammation in the cornea, reduction of the accumulation of Keratin proteins, particularly Keratin 13 and Keratin 4.

Advantages of this approach are numerous. One important advantage of the invention is the improvement in vision of patients at risk for or suffering from corneal opacification. Another advantage is that the invention provides for a non-invasive alternative to treatment of corneal opacification.

Definitions

Terms used in the claims and specification are defined as set forth below unless otherwise specified.

The term "proteasome modulator" refers to any chemical or drug composition or substance that leads to altered proteasome function, including altered proteasome activity or proteasome abundance in the subject.

The term "corneal opacification" includes conjunctivalization, corneal scarring and corneal conditions resulting in corneal haze, reduction in corneal transparency, increased globlet cells in the cornea, increased conjunctival proteins in the cornea, increased Muc5ac protein in the cornea or increased keratin proteins in the cornea.

The term "treatment" refers to a medical method for attempting to cause an improvement in the condition of a disease state, including prophylaxis, lessening in the severity or progression, remission, or cure thereof.

The term "in vivo" refers to processes that occur in a living organism.

The term "mammal" as used herein includes both humans and non-humans and include but is not limited to humans, non-human primates, canines, felines, murines, bovines, equines, and porcines.

The term "administration" refers to introducing an agent of the present disclosure into a host. One route of administration of the agents is oral administration. Another route is intravenous administration. However, any route of administration, such as topical, subcutaneous, peritoneal, intra-arterial, inhalation, vaginal, rectal, nasal, introduction into the cerebrospinal fluid, or instillation into body compartments can be used.

The term "vehicle control" broadly refers to any inert medium in which the active ingredient is administered, including but not limited to solvents, carriers or binders for the active ingredient.

The term "effective amount" is an amount that is sufficient to produce a desired effect, e.g., an amount to ameliorate a symptom of a condition or disease.

The term "formulation" includes pharmaceutical formulations comprising pharmaceutically acceptable salts, pharmaceutically acceptable excipients, pharmaceutically acceptable diluents, pharmaceutically acceptable carriers or pharmaceutically acceptable adjuvants.

Abbreviations used in this application include the following:
CPR=26S constitutive proteasome
IPR=immunoproteasome
LSCD=Limbal Stem Cell Deficiency
K13=Keratin 13
K4=Keratin 4
CEC=Corneal Epithelial Cells
CjEC=Conjunctival Epithelial Cell It must be noted that, as used in the specification and the appended claims, the singular forms "a," "an" and "the" include plural referents unless the context clearly dictates otherwise.

Methods of the Invention

Described herein are methods for treatment of corneal opacification by the present invention. Said methods of the invention include administering a therapeutically effective amount of a proteasome modulator, e.g., PS-341 (Bortezomib or Velcade® Millennium.

Compounds Used in the Methods of the Invention

The compounds used in the methods of the instant invention comprise commercially-available proteasome modulators. The commercially available proteasome modulators of the invention include, but are not limited to, MG-132, Bortezomib (PS-341), Dihydroeponemycin, Oprozomib (ONX-0912), MLN2238, Epoxomicin, Carfilzomib (PR-171), ONX-0914 (PR-957), PSI, MG-115, MG-262, AM 114, PI-1840, Chymotrypsin-like (CT-L) inhibitor, MLN9708, CEP-18770, Gliotoxin, Salinosporamide A (NPI-0052, Marizomib), Clasto-Lactacystin β-lactone, Lactacystin, Ixazomib™, oleuropein or derivatives or analogues thereof.

Pharmaceutical Compositions Used in the Methods of the Invention

The proteasome modulators used in the methods of the invention can be formulated in pharmaceutical compositions. These compositions can comprise, in addition to one or more of the proteasome modulators, a pharmaceutically acceptable excipient, carrier, buffer, stabiliser or other materials well known to those skilled in the art. Such materials should be non-toxic and should not interfere with the efficacy of the active ingredient. The precise nature of the carrier or other material can depend on the route of administration, e.g., topical, oral, intravenous, cutaneous or subcutaneous, nasal, intramuscular, intraperitoneal routes.

Pharmaceutical compositions for topical administration can be ophthalmic solutions, ophthalmic gel-forming solutions, ophthalmic suspensions, ophthalmic ointments, ophthalmic emulsions.

Pharmaceutical compositions for oral administration can be in tablet, capsule, powder or liquid form. A tablet can include a solid carrier such as gelatin or an adjuvant. Liquid pharmaceutical compositions generally include a liquid carrier such as water, petroleum, animal or vegetable oils, mineral oil or synthetic oil. Physiological saline solution, dextrose or other saccharide solution or glycols such as ethylene glycol, propylene glycol or polyethylene glycol can be included.

For intravenous, cutaneous or subcutaneous injection, or intraocular injection, the active ingredient will be in the form of a parenterally acceptable aqueous solution which is pyrogen-free and has suitable pH, isotonicity and stability. Those of relevant skill in the art are well able to prepare suitable solutions using, for example, isotonic vehicles such as Sodium Chloride Injection, Ringer's Injection, Lactated Ringer's Injection. Preservatives, stabilisers, buffers, antioxidants and/or other additives can be included, as required.

The pharmaceutically useful compound according to the present invention that is to be given to an individual, administration is preferably in a "therapeutically effective amount" or "prophylactically effective amount,", this being sufficient to show benefit to the individual. The actual amount administered, and rate and time-course of administration, will depend on the nature and severity of protein aggregation disease being treated. Prescription of treatment, e.g., decisions on dosage etc, is within the responsibility of general practitioners and other medical doctors, and typically takes account of the disorder to be treated, the condition of the individual subject, the site of delivery, the method of administration and other factors known to practitioners. Examples of the techniques and protocols mentioned above can be found in Remington's Pharmaceutical Sciences, 16th edition, Osol, A. (ed), 1980.

A composition can be administered alone or in combination with other treatments, either simultaneously or sequentially dependent upon the condition to be treated.

EXAMPLES

Below are examples of specific embodiments for carrying out the present invention. The examples are offered for illustrative purposes only, and are not intended to limit the scope of the present invention in any way. Efforts have been made to ensure accuracy with respect to numbers used (e.g., amounts, temperatures, etc.), but some experimental error and deviation should, of course, be allowed for.

The practice of the present invention will employ, unless otherwise indicated, conventional methods of protein chemistry, biochemistry, recombinant DNA techniques and pharmacology, within the skill of the art. Such techniques are explained fully in the literature. See, e.g., T. E. Creighton, *Proteins: Structures and Molecular Properties* (W.H. Freeman and Company, 1993); A. L. Lehninger, *Biochemistry* (Worth Publishers, Inc., current addition); Sambrook, et al.,

*Molecular Cloning: A Laboratory Manual* (2nd Edition, 1989); *Methods In Enzymology* (S. Colowick and N. Kaplan eds., Academic Press, Inc.); *Remington's Pharmaceutical Sciences*, 18th Edition (Easton, Pa.: Mack Publishing Company, 1990); Carey and Sundberg *Advanced Organic Chemistry* $3^{rd}$ *Ed.* (Plenum Press) Vols A and B (1992).

Methods

Rabbit Model of LSCD

New Zealand white rabbits weighing 2.5-3 kg were used. They were maintained according to the Guidelines of Animal Care, as described by the National Academy of Sciences and published by the Institute of Laboratory Animal Resources Commission on Life Sciences National Research Council. LSCD was surgically induced in rabbits (see Example 1). Briefly, rabbits were sedated, subjected to 360° lamellar limbectomy, and followed for 3 months until LSCD was confirmed stable by the ophthalmologist.

Impression Cytology

Millicell® culture inserts 12 mm diameter, 0.4 µm pore size, with mixed cellulose membrane (Millipore, Billerica, Mass.) were used to sample corneal epithelial cells. The inserts were placed on the cornea for few seconds, and then slowly removed. The inserts were then allowed to dry for 1 h at room temperature. The inserts were then fixed in 10% neutral buffered formalin overnight and conserved in 70% ethanol prior to immune-histochemical staining analysis. The membranes were stained with K13 in immunofluorescent analysis.

Corneal Epithelial Cells (CEC) and Fibro-Vascular Pannus Tissue (PT) Sampling

Rabbits were lightly sedated and corneal epithelial cells were sampled by exposing the corneas to 20% isopropyl alcohol for one minute to loosen up the corneal epithelium. The corneas were then washed 3 times with saline and CEC were harvested from the corneal surface and PT was excised and removed by the ophthalmologist using a crescent knife 2 mm angled, double bevel (Katena products, Inc; Denville, N.J.). CEC were suspended in PBS, centrifuged and then re-suspended in lysis buffer containing 20 mM Tris-HCl pH=7.5; glycerol 10% EGTA 1 mM; DTT 1 mM; protease and phosphatases inhibitor cocktail as instructed by the supplier (Sigma, St Louis, Mo.). Cell membranes were disrupted by 5 second of sonication. The samples were then frozen at −80° C. until all samples—healthy and LSCD's epithelial cells—were gathered for biochemical analysis.

Western Blot Analysis

Protein concentration was measured using the Bio-Rad protein assay. Two µg of total protein from lysed corneal epithelial cell samples and from harvested oral mucosa epithelial cell samples were separated by SDS-PAGE electrophoresis using 124-20% gradient polyacrylamide gels. Proteins were then transferred to a PVDF membrane (Bio-Rad, Hercules, Calif.) for 1 h in 25 mM Tris-HCl (pH=8.3), 192 mM Glycine and 20% methanol. Membranes were probed with primary antibodies against keratins K4 and K13 (Santa Cruz Biotechnology, Santa Cruz, Calif.). Goat anti-mouse and sheep anti-Goat antibodies (Bio-Rad, Hercules, Calif.) were used as secondary antibodies. Immuno-detection was done using ECL plus (Amersham Bioscience Corp., Piscataway, N.J.). Bands densitometric measurements were performed using the GS-800 imaging densitometer (Bio-Rad, Hercules, Calif.).

Immunohistochemistry

Normal and LSCD diseased corneal epithelial cells and oral mucosa epithelial cell specimens were fixed in 10% neutral buffered formalin. The processed tissues were sectioned, and the slides were stained in immunofluorescent staining. Mouse monoclonal antibodies against keratins K4 and K13 (Santa Cruz Biotechnology CA), goat polyclonal against ubiquitin (Santa Cruz Biotechnology) were used in single and double staining. K4 and K13 were detected with second antibody conjugated to Alexa Fluor® 488. Ubiquitin was detected with second antibody conjugated to Alexa Fluo® 568 donkey anti-goat. 4',6-diamidino-2-phenylindole (DAPI) (Thermo Scientific, Waltham, Mass.) was used for nuclear staining. The level of protein expression was examined using a Nikon 400 fluorescent microscope with FITC cube and a triple band cube to detect FITC, Texas Rex and DAPI. Picture processing and analysis was performed using Adobe Photoshop CS5.

Oral Mucosa Epithelial Cell Isolation, Cell Culture and Treatment with Proteasome Inhibitor Oral mucosal biopsy was performed on a sedated animal, using a 6 mm diameter disposable punch biopsy instrument (Biopunch HealthLink, Jacksonville, Fla.). The biopsy specimen was washed in sterile saline, sanitized in povidone iodine, washed again in sterile saline and then washed in DMEM cell culture media. The specimen was then used to isolate oral mucosal epithelial cells, as previously described [21]. Briefly, the specimen was minced and incubated with Dispase I for one hour at 37° C. (Roche Diagnostics GmbH, Mannheim, Germany), the epithelium was separated from the lamina propria and subjected to trypsin digestion to separate the epithelial cells. The isolated primary epithelial cells were then seeded at $5 \times 10^5$ density on Transwell insert (Corning Inc.), and co-cultured with mitomycin C (MMC)-treated NIH/3T3 feeder cells. After 4 days of cell culture, the media was changed and EGF was added at 10 ng/mL final concentration. Cell culture media was changed every two days. After two weeks of cell culture and when the cells grew to form a multilayered tissue like, proteasome inhibitor (PS-341, (Bortezomib/Velcade®, Millennium Pharmaceutical, a highly specific proteasome inhibitor) was added in cell culture media for 24 h and for 72 h at 2.5, 5, 10, 20, and 50 nM, to, respectively achieve proteasome inhibition or proteasome activation.

Proteasome Activity

One µg of total protein from sample homogenates was used. The reaction mixture contained 50 mM Tris-HCl pH=8, 1 mM DTT, and 40 µM Suc-Leu-Leu-Val-Tyr-AMC (Sigma Aldrich) substrate for chymotrypsin-like activity or 40 µM of Boc-Leu-Ser-Thr-Arg-AMC for trypsin-like activity or 100 uM of Ac-Gly-Pro-Leu-Asp-AMC (Sigma Aldrich) for Caspase-like activity. 5 mM ATP was added to the reaction mixture to distinguish 26S proteasome activity from 20S proteasome activity. The mixture was then incubated for 30 min at 37° C., and then stopped by adding 100 µM monochloroacetate and 30 mM sodium acetate pH=4.3. Fluorescence was determined by measuring the release of AMC ($\lambda$, excitation: 370 nm, $\lambda$, emission: 410 nm), using a Perkin Elmer LS 30 spectrofluorometer.

Statistics

Data were obtained from at least three separate experiments. Bars represent mean values ±SEM. P values are determined by one-way ANOVA and Student-Newman Keuls for multiple group comparisons (Sigma-Stat softdish, San Francisco, Calif.). Statistical significance is set at p= or < to 0.05. Bar graphs were shown as Mean±SEM, n=3-4.

Example 1: LSCD-Induced Model of Opacification

Figure 1:
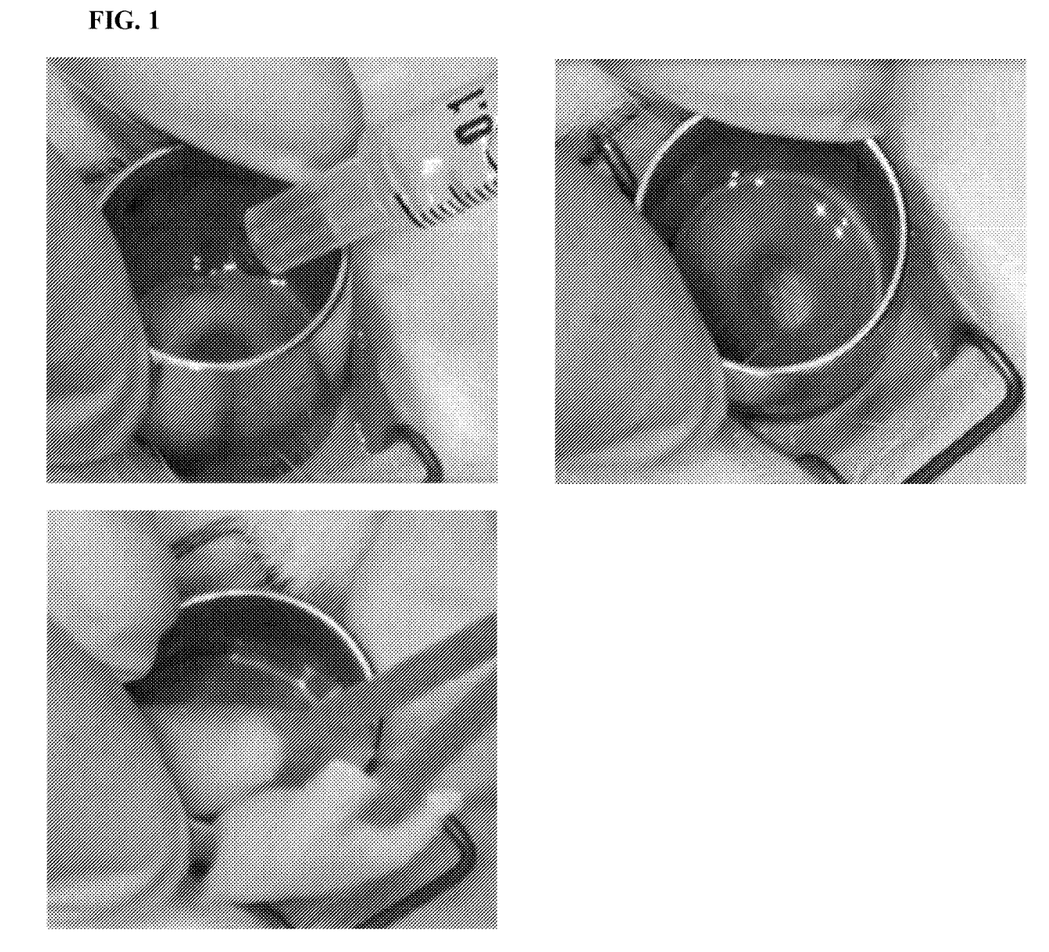
FIG. 1 describes the LSCD-induced model opacification and application of PS-341 to the central cornea to ensure only central cornea is exposed to topical application of PS-341.

Our model of LSCD-induced opacification achieved total removal of limbal stem cells and obtained stable LSCD. The experimental protocol was performed according to the following schedule: 1) administration of anesthesia, 2) perform lamellar limbectomy to create LSCD, 3) follow up for 3 months until the pathology is stable, 4) administer PS-341 treatment by topical administration (FIG. 1) of the predetermined optimal dose of PS-341 every 72 hours for one month. Based on our in vitro study, one drop of PS-341 optimal dose was administered every 72 hours for one month. Corneas were routinely examined in the scheduled follow ups. 5) Grading of corneal opacification was performed based on the visibility of the iris details and scored as: Grade 0: clear cornea with visible iris details; Grade 1: mild opacification with less distinct iris details; Grade 2: moderate opacification if the iris is poorly visible; Grade 3: severe opacification if the iris is not visible and the cornea is totally opaque. 6) Rabbits were sacrificed and cornea tissue, including corneal epithelial cells and fibro-vascular pannus tissue was collected for histological analysis and to score the effects of PS-341 (K4/K13 staining). PS341 treatment of the central cornea was performed by exposing the cornea to topical application of PS 341. A trephine was used to limit PS 341 exposure to only the central cornea so that only modified K13 and/or K4 is cleared without any effect on endogenous K13 and on the conjunctival epithelium integrity (FIG. 1).

Figure 2A:
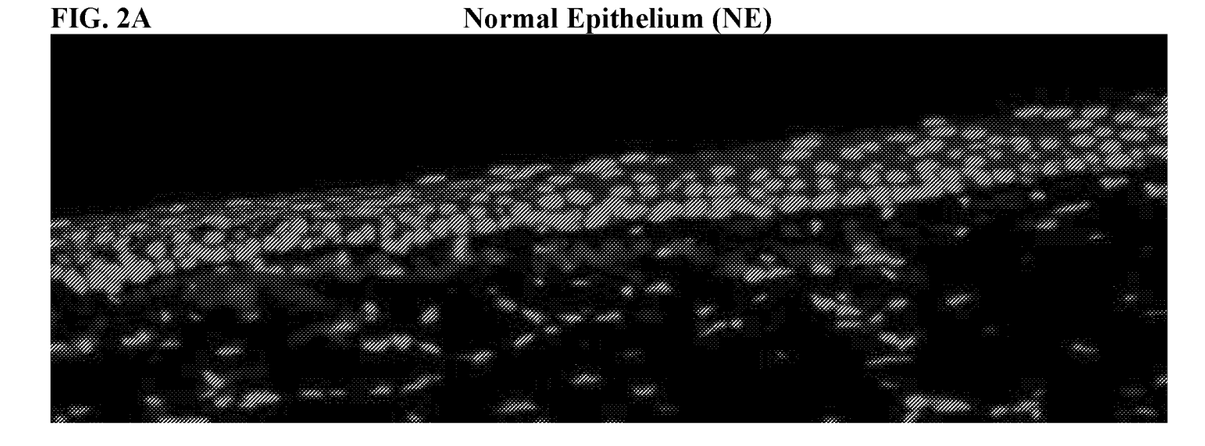
FIG. 2A shows K13 staining in normal corneal epithelium (NE).
Figure 2B:
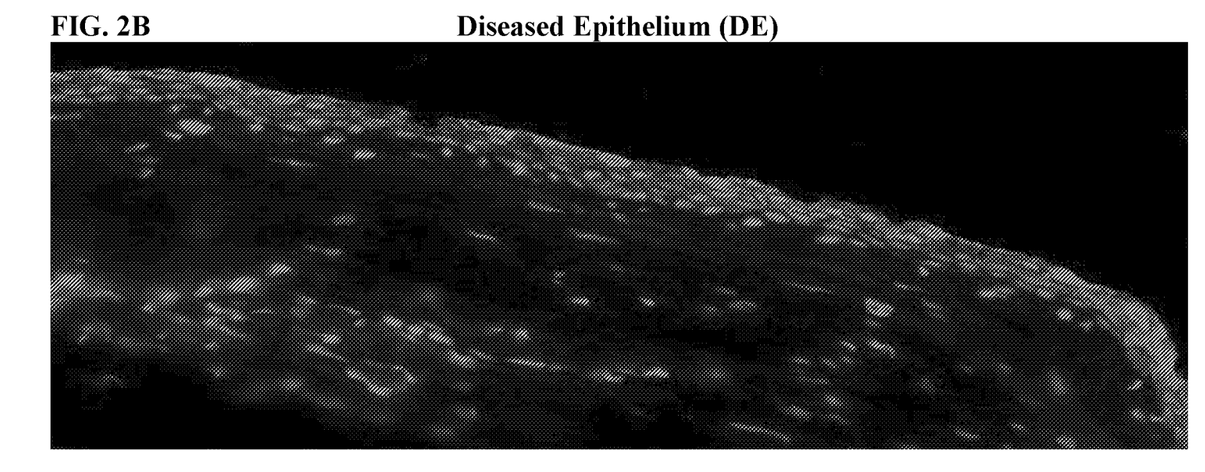
FIG. 2B shows the central cornea is covered with Keratin 13 in a LSCD-induced model of opacification (DE) 3 months after corneal injury.
Figure 3A:
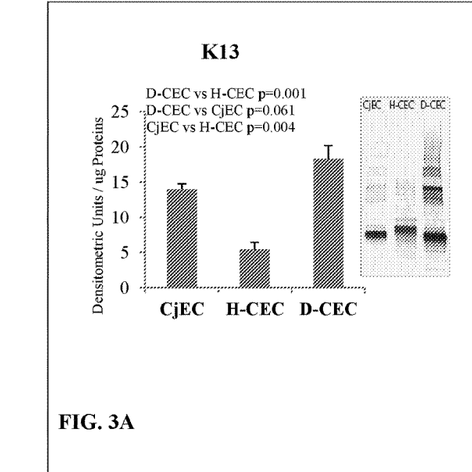
FIG. 3A shows K13 levels are increased 3 months after corneal injury.
Figure 3B:
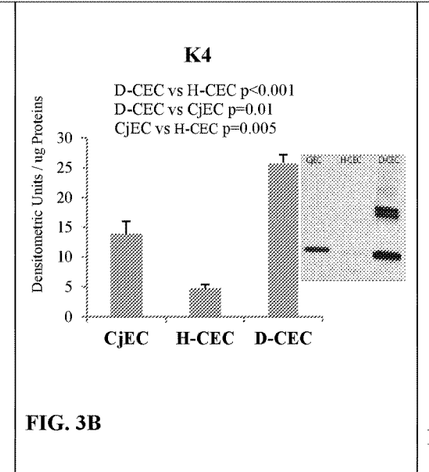
FIG. 3B shows K4 levels are increased 3 months after corneal injury.
Figure 3C:
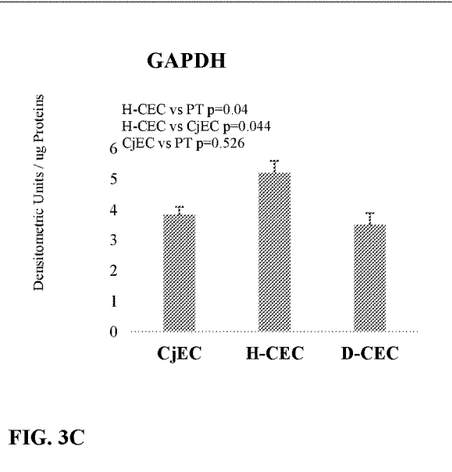
FIG. 3C shows GAPDH levels 3 months after corneal injury.
Figure 3D:
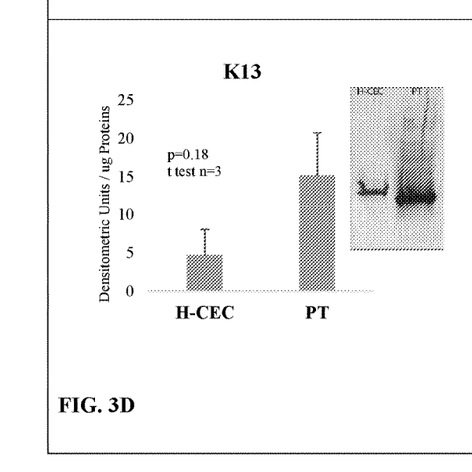
FIG. 3D shows K13 levels 3 months after corneal injury in pannus tissue (PT).
Figure 3E:
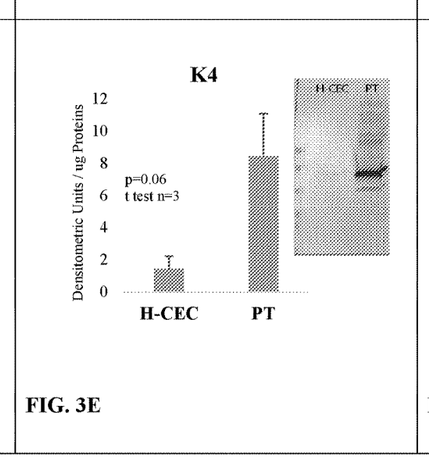
FIG. 3E shows K4 levels 3 months after corneal injury in pannus tissue (PT).
Figure 3F:
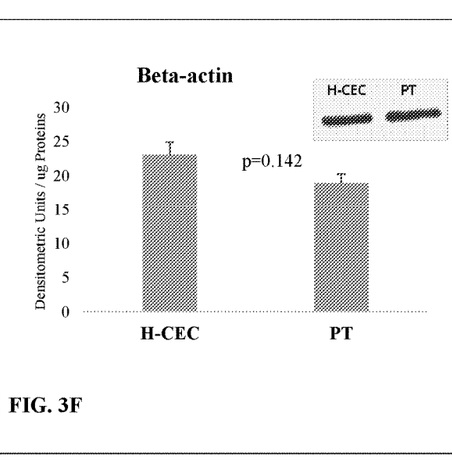
FIG. 3F shows beta-actin levels 3 months after corneal injury in pannus tissue (PT).

Example 2: The Central Cornea is Covered with Keratin 13 and Keratin 4 in a LSCD-Induced Model of Opacification Results from histopathological examination of the LSCD-induced opacification model showed that while normal cornea stained K13 positive only on the conjunctival side, K13 markedly covered central cornea of LSCD diseased cornea, as shown by the cytoplasmic cellular staining on the top of the tissue sections in FIGS. 2A and 2B, respectively. K4 was also detected in the conjunctiva-limbal area and central cornea of LSCD diseased cornea (data not shown). In addition, pannus tissue harvested from the LSCD diseased cornea was found positive for K4 (data not shown). The results show that the central cornea is covered with K13 and K4 in corneas from animals with LSCD and not in normal cornea. There was K13 and K4 accumulation with additional higher molecular weight bands in diseased corneal epithelial cells (D-CEC) compared to healthy corneal epithelial cells (H-CEC) indicating K13 and K4 posttranslational modifications and suggesting ubiquitination of K13 is associated with CPR failure in diseased epithelium (FIGS. 3A-3C). Pannus tissue (PT) harvested from the LSCD diseased cornea also demonstrated increased K13 and K4 (FIGS. 3D-3F).

Example 3: CPR Proteasome Activity is Decreased in LSCD Corneal Epithelium

Figure 4:
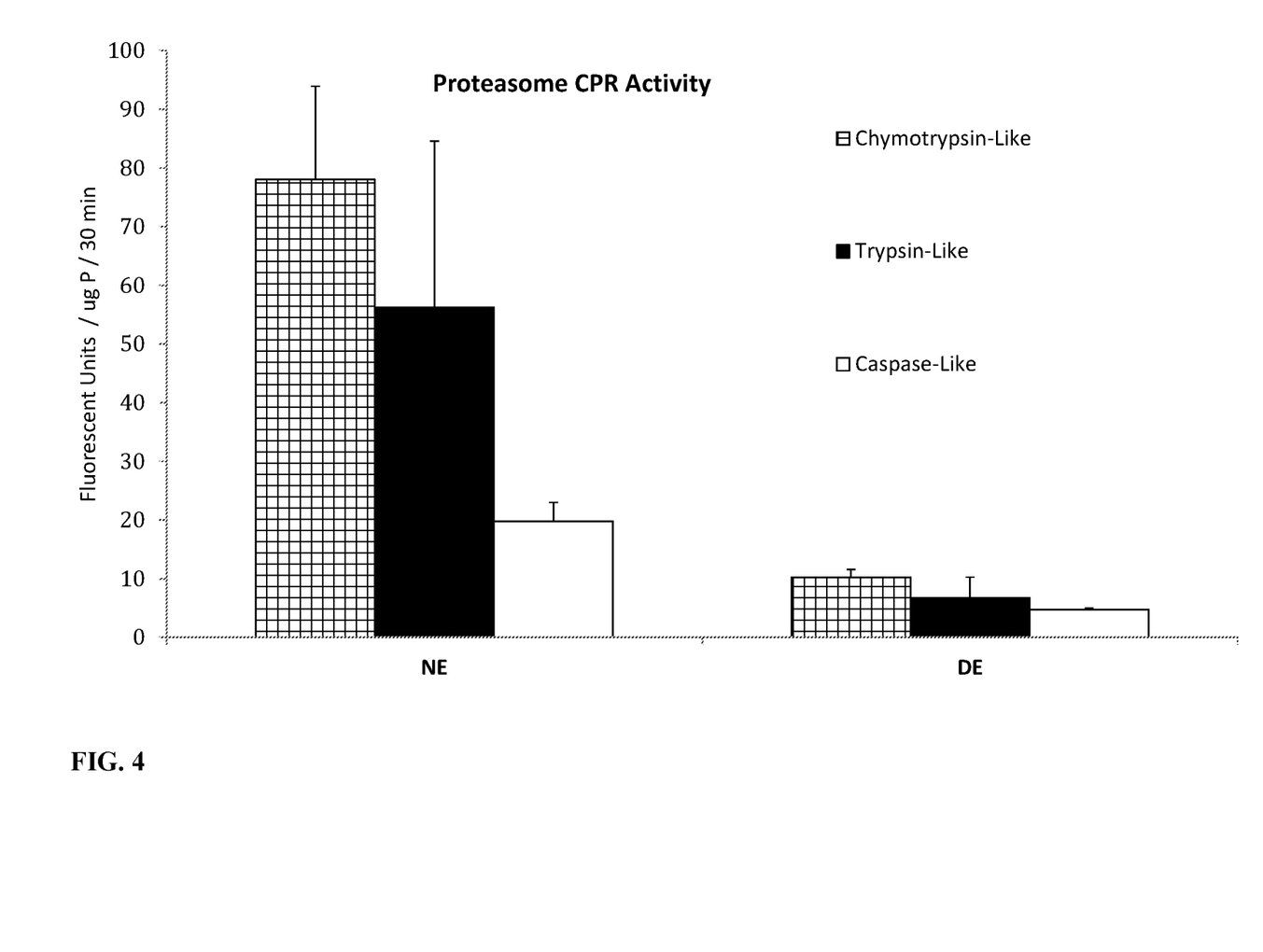
FIG. 4 shows CPR activity is significantly decreased in corneal diseased epithelium.
Figure 5A:
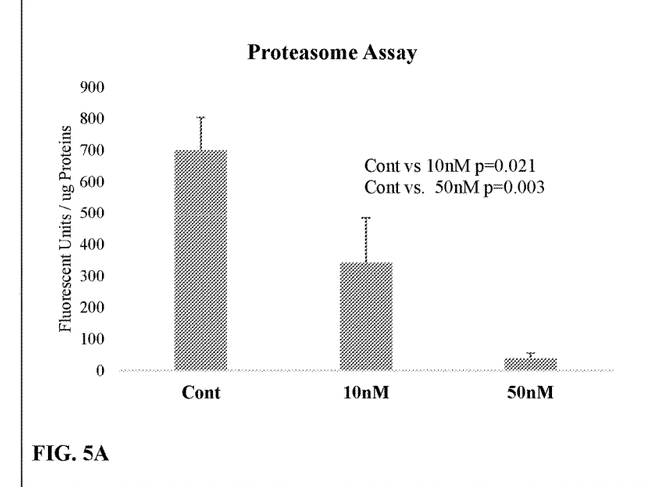
FIG. 5A shows CPR activity is significantly decreased in oral mucosa epithelial cells treated with high dose of PS-341.
Figure 5B:
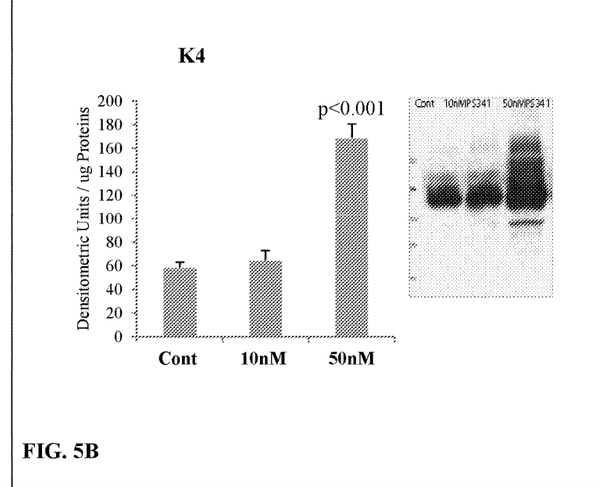
FIG. 5B shows K4 levels are increased in oral mucosa epithelial cells treated with high dose of PS-341.
Figure 5C:
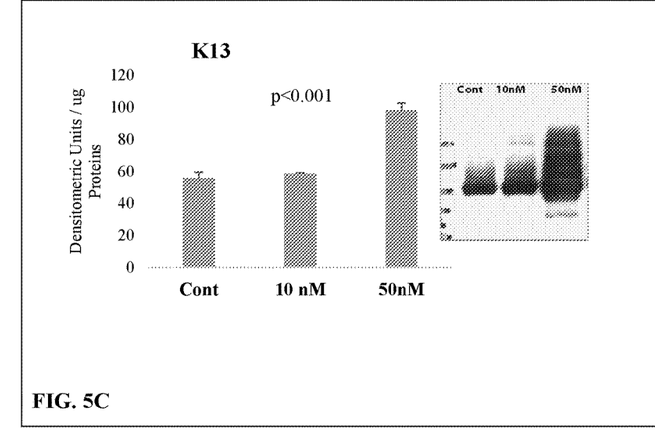
FIG. 5C shows K13 levels are increased in oral mucosa epithelial cells treated with high dose of PS-341.
Figure 5D:
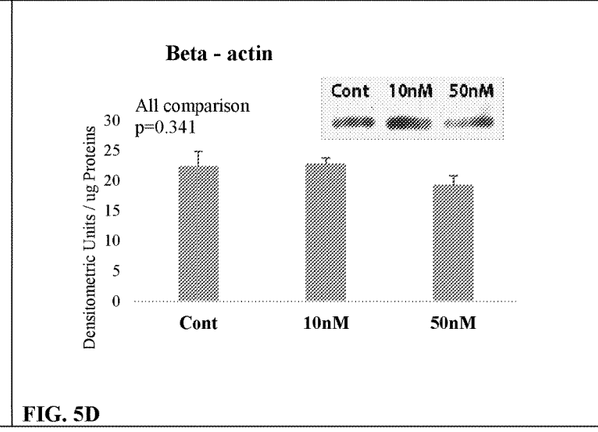
FIG. 5D shows beta-actin levels in oral mucosa epithelial cells treated with high dose of PS-341.

Experiments made on collected corneal epithelial cells from LSCD rabbits showed that all CPR activities were significantly decreased in corneal diseased epithelium (DE) (FIG. 4).

Example 4: K4 and K13 are a Substrate for CPR

To further substantiate the role of CPR dysfunction in K13 accumulation, rabbit oral mucosa epithelial cells (OMECS), which express K4/K13 similar to conjunctival epithelial cells, were cultured and treated with proteasome inhibitor PS-341 (Bortezomib/Velcade®) at high doses using 10 and 50 nM final concentration for 24 hours before harvesting cells. FIG. 5 shows that when OMECS were treated with high doses of CPR inhibitor, Chymotrypsine-like proteasome activity decreased and K4 and K13 were modified and significantly accumulated. Moreover, proteasome pulldown fractions stained positive for K13 (data not shown). These results demonstrated that K4 and K13 are a substrate for CPR.

Since all proteins to be degraded by the proteasome are tagged with ubiquitin, we conducted double staining experiments to analyze whether keratins were ubiquitinated in OMECS treated with PS-341 (data not shown). There was a reproducible co-localization of K4 and K13 with ubiquitin, indicating that both K4 and K13 are ubiquitinated.

Figure 6:
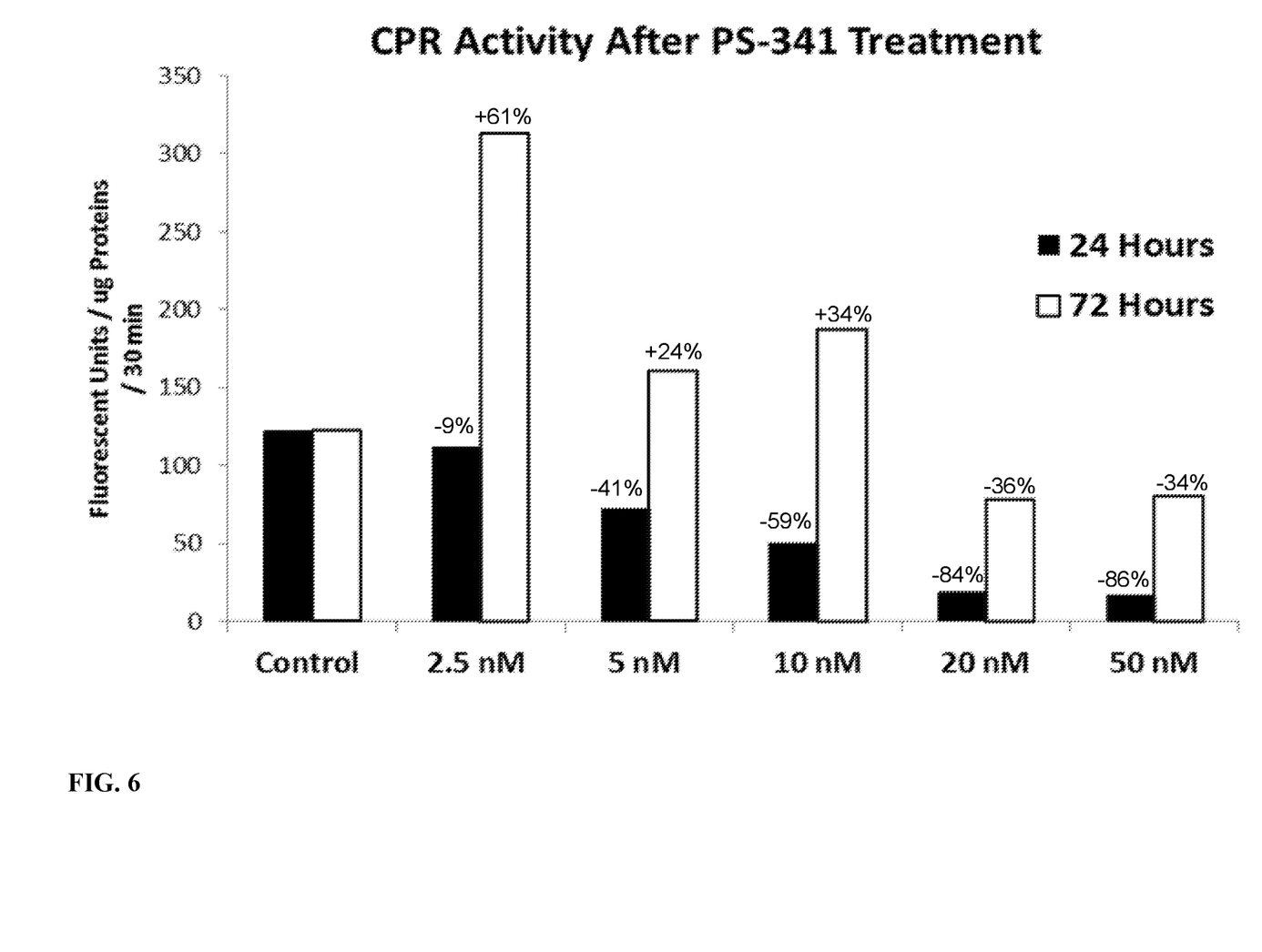
FIG. 6 shows treatment of cells with low doses of proteasome modulator PS-341 leads to rebound of proteasome activity 72 hours after treatment with PS-341.
Figure 7A:
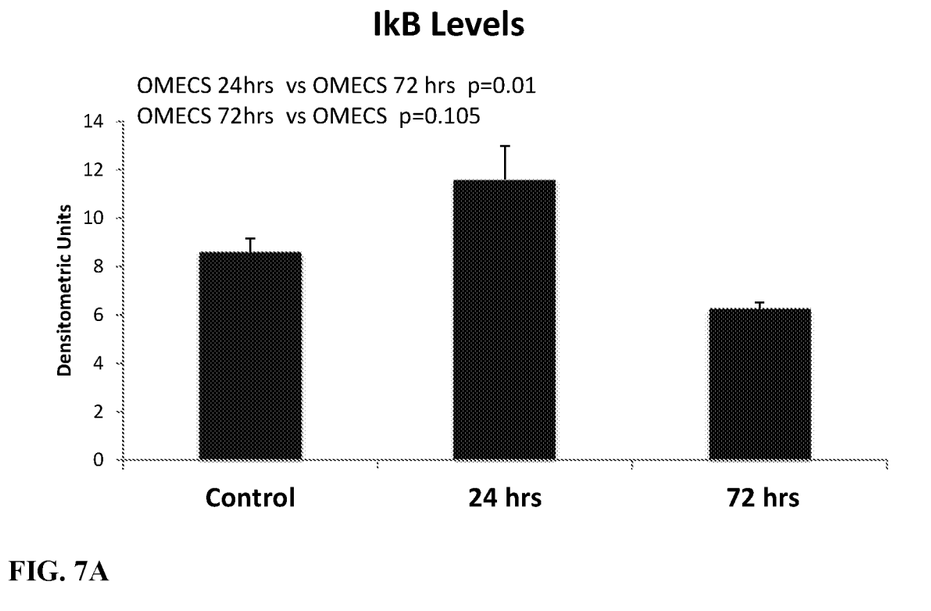
FIG. 7A shows decreased levels of expression of Inhibitor Kappa B 72 hours after treatment of oral mucosa epithelial cells (OMECS) with 2.5 nM of PS-341.
Figure 7B:
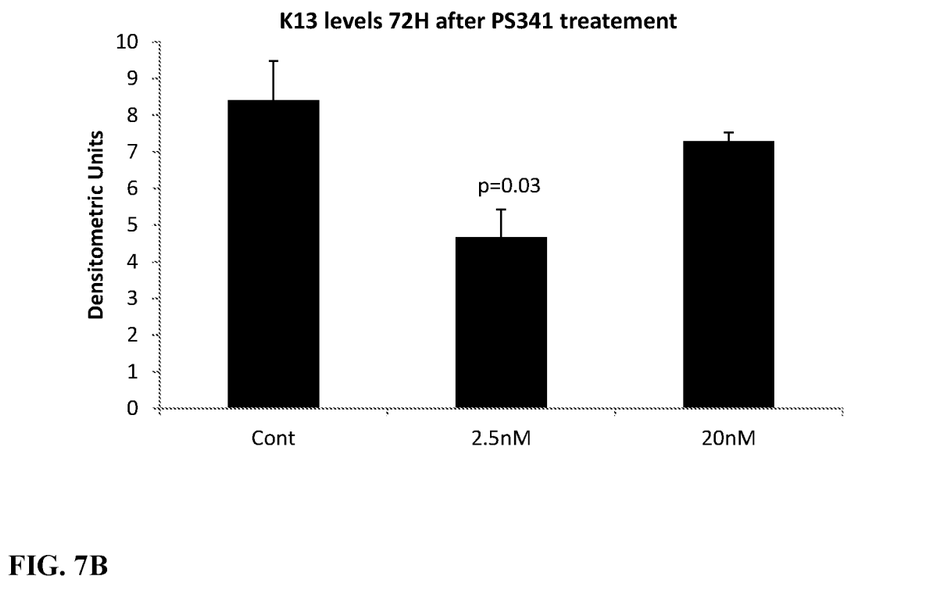
FIG. 7B shows decreased levels of expression of K13 72 hours after treatment of OMECS with 2.5 nM of PS-341.
Figure 7C:
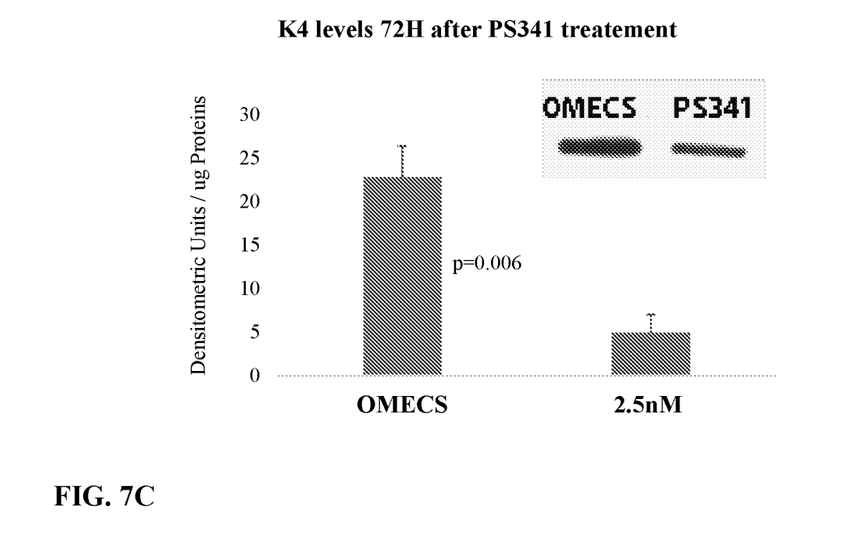
FIG. 7C shows decreased levels of expression of K4 72 hours after treatment of OMECS with 2.5 nM of PS-341.
Figure 7D:
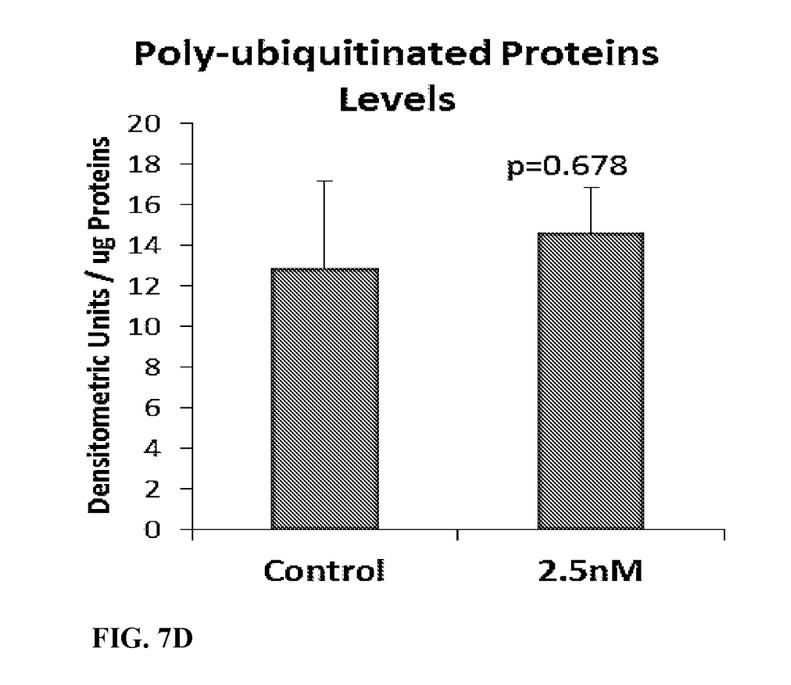
FIG. 7D shows levels of polyubiquitinated proteins 72 hours after treatment of OMECS with 2.5 nM of PS-341.
Figure 7E:
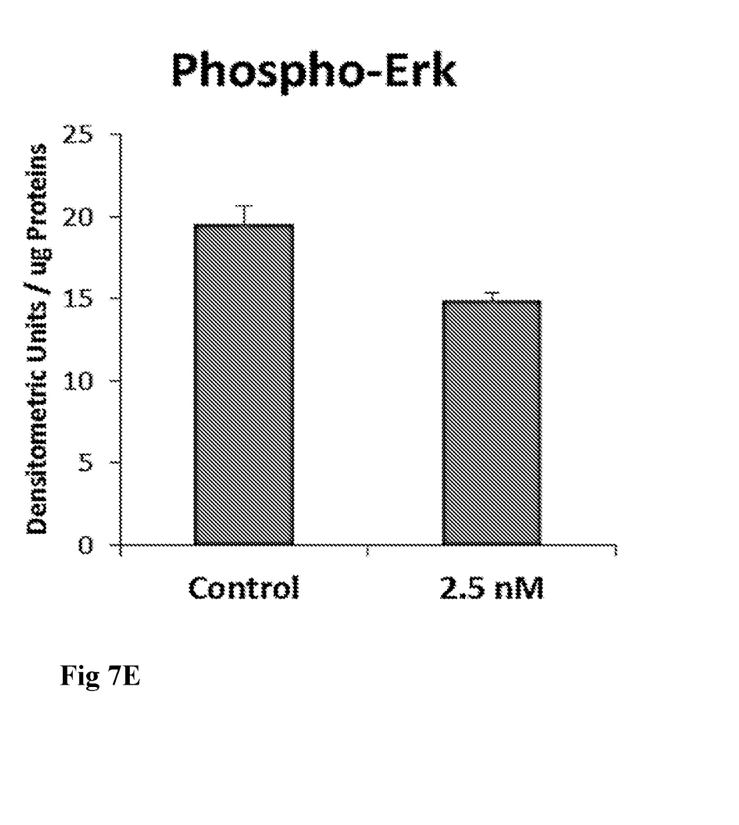
FIG. 7E shows decreased levels of phosphorylated ERK in OMECS 72 hours after treatment with 2.5 nM of PS-341.

Example 5: Treatment with Non-Toxic Doses of Proteasome Inhibitor Results in Rebound of Proteasome Activity and Reduction of K13 and K4 Levels The beneficial effects of proteasome inhibitor treatment reside in the reversibility of the drug and in the rebound of proteasome activity 72 hours after PS-341 treatment, as demonstrated in cultured rabbit oral mucosal epithelial cells (FIG. 6). Oral mucosa epithelial cells were treated with PS-341 for 24 hours and for 72 hours at 2.5, 5, 10, 20, and 50 nM. At 24 h, all PS-341 doses lead to CPR chymotrypsin-like activity decrease (9%, −41%, −59%, −84% and −86%, respectively. At 72 hours, 2.5 nM, 5 nM and 10 nM were the only doses that increased proteasome activities. 2.5 nM showed the highest increase in proteasome chymotrypsin-like activity which was 61% higher than untreated cells. Treatment with 2.5 nm of PS-341 also decreased inflammation by stabilizing IκB in the first 24 hours, which, in turn, blocked NFκB activation (FIG. 7A) and consequently decreased K13 and K4 levels in PS-341-treated OMECS (FIGS. 7B and 7C). Western blot analysis of cells treated with 2.5 nM of PS-341 for 72 h showed no significant poly-ubiquitinated protein accumulation (FIG. 7D) and no significant change in phospho-Erk levels (FIG. 7E), suggesting the lack of an apoptotic signal and indicating that the treatment, at this very low dose, does not produce toxic effects. Therefore, treatment of cells with a low dose of proteasome inhibitor results in prolonged increase in proteasome rebound activity leading to the degradation of keratin proteins.

While the invention has been particularly shown and described with reference to a preferred embodiment and various alternate embodiments, it will be understood by persons skilled in the relevant art that various changes in form and details can be made therein without departing from the spirit and scope of the invention.

All references, issued patents and patent applications cited within the body of the instant specification are hereby incorporated by reference in their entirety, for all purposes.

REFERENCES CITED

1. Bardag-Gorce F, Riley N E, Nan L, Montgomery R O, Li J, French B A, Lue Y H, French S W. The proteasome inhibitor, PS-341, causes cytokeratin aggresome formation. Exp Mol Pathol. 2004; 76 (1):9-16.
2. Bardag-Gorce F, Oliva J, Wood A, Hoft R, Pan D, Thropay J, Makalinao A, French S W, Niihara Y. Carrier-free cultured autologous oral mucosa epithelial cell sheet (CAOMECS) for corneal epithelium reconstruction: a histological study. Ocul Surf 2015; 13(2):150-63.

3. Lin C T, Hu F R, Kuo K T, Chen Y M, Chu H S, Lin Y H, Chen W L. The different effects of early and late bevacizumab (Avastin) injection on inhibiting corneal neovascularization and conjunctivalization in rabbit limbal insufficiency. Invest Ophthalmol Vis Sci. 2010.

4. Poli M, Burillon C, Auxenfans C, Rovere M R, Damour O. Immunocytochemical Diagnosis of Limbal Stem Cell Deficiency: Comparative Analysis of Current Corneal and Conjunctival Biomarkers. Cornea. 2015; 34(7):817-23.

The invention claimed is:

1. A method of treating diseased corneal epithelium caused by Limbal Stem Cell Deficiency (LSCD) and characterized with keratin aggregation in a subject, comprising administering to the subject an effective amount of PS-341 (Bortezomib).

2. The method of claim 1, wherein the PS-341 is formulated as an ophthalmic preparation.

3. The method of claim 2, wherein the PS-341 is administered once every 72 hours.

4. The method of claim 2, wherein the PS-341 is administered once every 48 hours.

5. The method of claim 2, wherein the PS-341 is administered once every 24 hours.

6. A method for reducing keratin aggregation in the cornea caused by Limbal Stem Cell Deficiency (LSCD) in a subject in need thereof, comprising administering to the subject an effective amount of PS-341 (Bortezomib).

7. A method of treating diseased corneal epithelium caused by Limbal Stem Cell Deficiency (LSCD) and characterized with keratin aggregation in the cornea in a subject comprising administering to the subject an effective amount of PS-341 formulated as an ophthalmic preparation and administered every 24 to 72 hours, wherein the method results in reduced levels of Keratin proteins in the cornea of the subject as compared to before the administration.

* * * * *